(12) United States Patent
Wiggli et al.

(10) Patent No.: US 7,264,432 B2
(45) Date of Patent: Sep. 4, 2007

(54) DEVICE AND METHOD FOR TRANSFERRING OBJECTS

(75) Inventors: Markus Wiggli, Tann (CH); Hanspeter Romer, Wolfhausen (CH); Peter Muerset, Studen (CH); Gregor Batliner, Ottikon (CH); Fred Schinzel, Maennedorf (CH); Alois Oberholzer, Wald (CH)

(73) Assignee: Tecan Trading AG, Mannedorf (CH)

( * ) Notice: Subject to any disclaimer, the term of this patent is extended or adjusted under 35 U.S.C. 154(b) by 216 days.

(21) Appl. No.: 10/886,887

(22) Filed: Jul. 8, 2004

(65) Prior Publication Data

US 2005/0053454 A1    Mar. 10, 2005

(30) Foreign Application Priority Data

Jul. 11, 2003    (CH) .................................... 1217/03

(51) Int. Cl.
*B65H 5/00*    (2006.01)
(52) U.S. Cl. ............... 414/222.01; 269/73; 414/277; 414/806
(58) Field of Classification Search ........... 414/222.01, 414/222.12, 274, 277, 225, 280, 286, 800, 414/806; 198/347.1, 347.2, 348.2; 269/73; 209/577, 583
See application file for complete search history.

(56) References Cited

U.S. PATENT DOCUMENTS 6,060,022 A    5/2000    Pang et al.

2002/0018705 A1*    2/2002    Kawaguchi ................. 414/274
2003/0185656 A1*    10/2003    Hansl ......................... 414/277

FOREIGN PATENT DOCUMENTS

EP    0 629 858    10/1993
WO    WO92/22800    12/1992

OTHER PUBLICATIONS

Genisis Series Leaflet, Robotic Sample Processors, Apr. 1999.
Orca Trac Leaflet, Tecan Robotic Assay Composer.
Velocity 11 Leaflet, The Speed of Discovery, 2004.

* cited by examiner

*Primary Examiner*—Donald Underwood
(74) *Attorney, Agent, or Firm*—Notaro & Michalos PC

(57) ABSTRACT

A device for transferring and characterizing objects positions the object on a horizontal work field. The device includes at least one rail extending parallel to the X direction and a displacement unit, movable back and forth in the X direction, having a motorized gripping mechanism for grasping an object. A processor for controlling movements of the displacement unit and actions of the gripping mechanism is distinguished in that the displacement unit includes a carrying device, movable together therewith along the rail, for transferring objects in the X direction. The carrying device is a plate for carrying objects moved onto this carrying plate using the gripping mechanism. According to a method of the invention, objects are moved onto the plate of the carrying device, transferred in the X direction, and deposited again at a second position.

17 Claims, 2 Drawing Sheets

DEVICE AND METHOD FOR TRANSFERRING OBJECTS

FIELD AND BACKGROUND OF THE INVENTION

The present invention relates to devices and methods, according to the preambles of the claims and for transferring objects in a sample manipulation system, in which the objects are positioned on at least one essentially horizontal work field having a lengthwise dimension X and a transverse dimension Y.

Devices and systems are known, for use in assaying genes ("genomics"), proteins ("proteomics"), for discovering new active substances ("drug discovery"), and in clinical diagnosis ("clinical diagnostics"), which include, for example, a liquid handling robot and an object transfer robot. Such a system is, for example, the work platform distributed by the present applicant under the name "Genesis Robotic Sample Processor". This is a device for manipulating samples in containers and/or on specimen carriers (e.g., slides), the container and/or slide being positioned on an essentially horizontal work field having a lengthwise dimension X and a transverse dimension Y and the device including robot manipulators for manipulating the samples. This manipulation may relate to receiving and/or delivering fluids, particularly liquids, e.g., within this X-Y field. In addition, centrifuges and other processing stations or analysis stations for samples, such as fluorescence readers and the like, may be provided.

For such work platforms, the identification of objects, such as sample tubes, microplates, and other containers containing samples, is important. "Carriers", which are typically implemented for accommodating three microplates, are also referred to here as objects.

Such known work platforms include at least one rail extending parallel to the X direction and at least one displacement unit, movable back and forth in the X direction on this rail using drives, having a tool for characterizing an object and a motorized gripping mechanism for grasping and moving an object toward the characterization tool. Furthermore, this device includes a processor for controlling the motions of the displacement unit and the actions of the gripping mechanism and for processing the information provided by the characterization tool. The tool is typically implemented as a barcode reader and positioned on the displacement unit in the known work platforms.

Samples which are to be processed and/or assayed are typically located in tubes or in the wells of microplates. Such tubes are placed in suitable holders, so that each holder may accommodate a row of tubes which are positioned next to one another in a line in the Y direction, i.e., in the direction of the transverse dimension of the work platform. These holders are displaceably guided on the work area. Samples may also be located in the wells of microplates and/or may be pipetted out of the sample tubes into these wells. In this case, three microplates are typically positioned on one "carrier", which is also displaceably guided on the work area.

To check the identity of the samples in a tube holder or on a carrier, this tube holder or carrier is grasped with a gripper and pulled into the measurement region of the barcode reader. After the identification, the checked objects, i.e., the tube holder having the sample tubes and/or the carrier having the microplates, are pushed back again to their original location on the work area.

Such work platforms have proven themselves in many ways. However, the necessity often arises of transferring individual tubes, tube holders, microplates, or carriers to another position on the work area and/or the work field of the work platform.

This is typically performed by hand, on conveyor belts, or even using a robot manipulator, for example, which may move on the same rails as a liquid handling arm used for pipetting liquids.

Such a work platform is also known from U.S. Pat. No. 6,060,022 and is described as an automated system for processing samples. Depending on the complexity of the system and the process steps to be executed therewith, such a system may have multiple robot manipulators.

It has been shown that such robot manipulators must be used frequently enough that one must often wait for their availability to transfer objects on the work area of the work platform. In addition, the necessary identification of the samples represents complex work, which may slow down the operation of such a work platform.

SUMMARY OF THE INVENTION

According to a first aspect, the object of the present invention is to suggest alternative devices and methods, using which the transfer of samples in a work platform may be rationalized. According to a second aspect, the present invention relates to the additional identification and/or characterization of samples in a work platform.

According to the present invention, this object is achieved in regard to the first aspect by the combinations of features of the independent claims. Additional features, variations, and improvements according to the present invention, as well as an achievement of the object in regard to the second aspect, result from the dependent claims.

BRIEF DESCRIPTION OF THE DRAWINGS

Preferred embodiments of the present invention will be described in greater detail on the basis of schematic figures, without this restricting the scope of the present invention.

DESCRIPTION OF THE PREFERRED EMBODIMENTS

Figure 1:
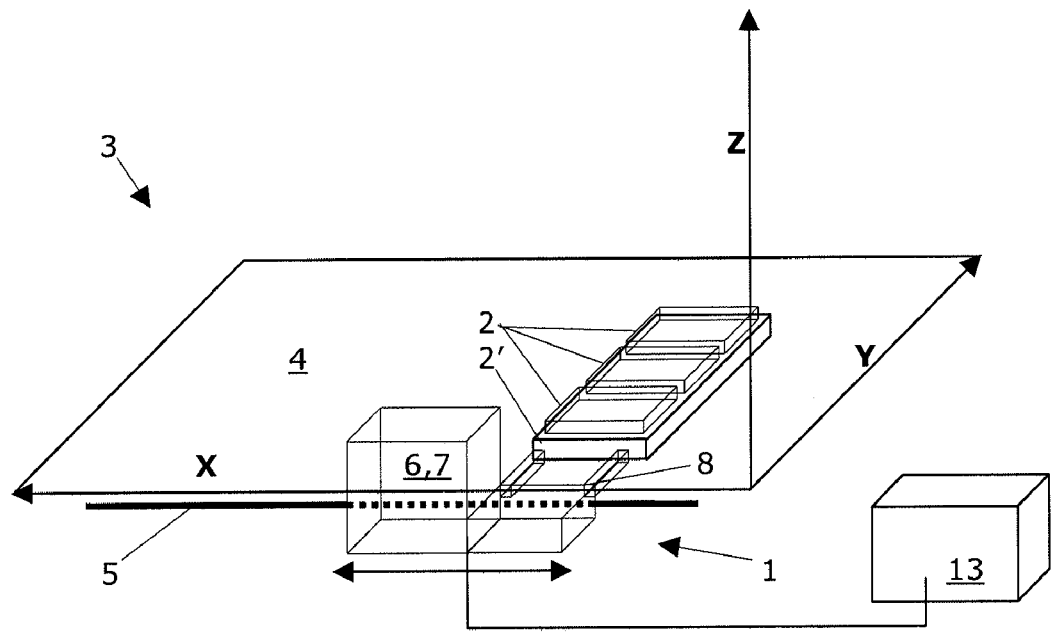
FIG. 1 shows a three-dimensional schematic diagram of a known work platform from the related art.

FIG. 1 shows a device 1 for characterizing objects 2 in a sample manipulation system 3, in which the objects 2 are positioned on at least one essentially horizontal work field 4 having a lengthwise dimension X and a transverse dimension Y. This device 1 includes at least one rail 5 extending parallel to the X direction and at least one displacement unit 6, which is movable back and forth in the X direction on this rail 5 using drives. The displacement unit preferably includes a tool 7 for characterizing an object 2 and a motorized gripping mechanism 8 for grasping and moving an object 2 toward the characterization tool 7. In addition, the device 1 includes a processor 13 for controlling the movements of the displacement unit 6 and the actions of the gripping mechanism 8 and for processing the information provided by the characterization tool 7.

Figure 2:
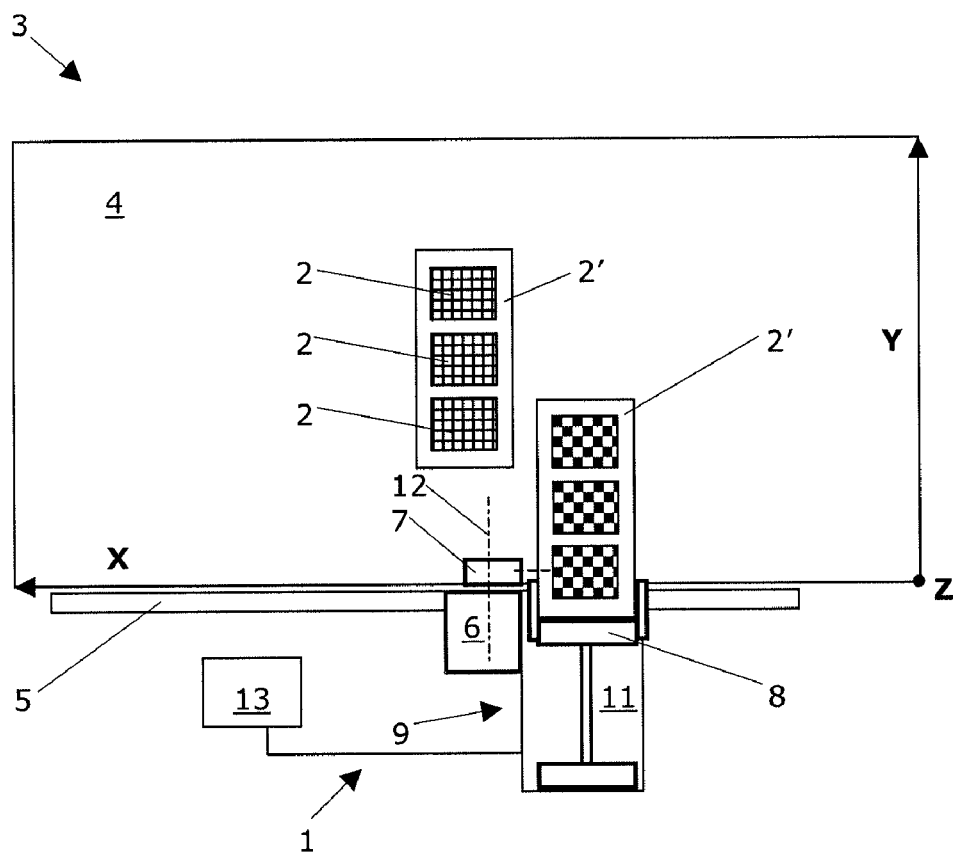
FIG. 2 shows a schematic top view of a first embodiment of a device according to the present invention.

FIG. 2 shows a schematic top view of a preferred first embodiment of a device 1 according to the present invention. This device includes, in addition to the elements of the work platform shown in FIG. 1, a displacement unit 6 having a carrying device 9, which is movable together with this displacement unit along the rail 5, for transferring objects 2 in the X direction. The carrying device 9 is implemented here as a carrying plate 11, which is movable along the rail 5 together with the displacement unit 6, the tool 7 for characterizing an object 2, and a motorized gripping mechanism 8 for grasping and moving an object 2 toward the characterization tool 7. Using the gripping mechanism 8, objects 2, whether they are carriers (as shown in FIG. 2), microplates, tube holders, troughs, or other containers for samples or liquids, are pulled onto the carrying plate 11 and transferred in the X direction on this carrying device 9.

It is obvious that the barcode reader used here as the characterization tool 7 scans one side of the first microplate 2 and/or one side of the carrier 2' and thus determines the identity of the samples in the corresponding wells. This identification is preferably performed while the carrier 2' is pulled onto the carrying plate 11 of the carrying device 9.

The received object is assignable to its original position on the work area 4 in accordance with the current X position of this carrying plate 11. This detection of the X position of the carrying plate 11, and the movement path of the gripping mechanism 8 to grasp the object (original Y position of the object), is performed via suitable sensors for detecting linear movements, as are known to those skilled in the art from the related art. The processing of the information from these sensors (not shown in FIG. 2), the control of the drives for the movement of the carrying plate 11 in the X direction and the gripping mechanism 8 in the Y direction, and the assignment of this information to an original X/Y position of the object is preferably performed in a digital computer (not shown), which is part of the sample manipulation system 3 or may be provided thereto.

In the meantime, manufactures and users of such work platforms have accustomed themselves to a hierarchical classification of the objects, at one end of which are the carriers and at the other end of which is always the container representing one single container. Multiple containers ideally form a two-dimensional field, array, or rack, in the form of a microplate, for example. Multiple (e.g., three) such racks have a defined position on a carrier. Particularly if all objects are variable, the identification of all objects of the entire hierarchy is desirable and advantageous. It may also be important to track individual wells of a microplate via software applications. However, because of the defined position of all wells within such an object, it suffices to identify the microplate itself perfectly.

If sample tubes are used as the containers, individual tubes may be replaced at practically any time (by hand or with the aid of a robot arm) and therefore are also to be identified individually for the sake of safety.

The hierarchy just described also plays a role in the scope of the present invention: the barcode reader used in FIG. 2 as the characterization tool 7 preferably simply travels along the rail 5 in a first passage and reads the identification marks or flags of the carriers, which are preferably all readable essentially vertically from the rear. On the basis of this data it is recognized, for example, which types of carriers these are and whether they may simply be pulled onto the platform surface in the event of a later transfer. Preferably, it may also be inferred from this data whether and at which positions and angles the corresponding barcodes of the objects positioned on the carrier are to be expected. In a second passage, if needed, the actual content of the objects is identified, the following assignments being made, for example: tubes to patient data; reagents to control; microplates to control and allocation. Therefore, a double identification is preferably performed first in each case as a standard and only later (if necessary) does one switch over to a direct recheck.

The gripping mechanism 8 is implemented here as a telescopic arm; as an alternative to this, it may also be implemented as an articulated arm. A further alternative embodiment of the gripping mechanism (not shown) includes a rail running in the Y direction having a caterpillar tread, which may be raised and/or lowered in order to grasp and/or deposit the carrier, for example. Using this carrying device 9, an object 2, which was moved toward the characterization tool 7, may be transferred in the X direction and then deposited using the gripping mechanism 8 at a position on the work field which is different from the original position of the object on the work area. At the same time, as the gripping mechanism 8 is moved out, the identity of the samples and/or the objects is preferably detected once again and the new X/Y position of this object 2, 2' is stored in the central computer.

From the previous description, it may be seen that objects 2 may not only be grasped, transferred in a plane, and deposited again using the gripping mechanism 8; rather, objects 2 may also be transferred from one plane to a plane positioned above or below it in the Z direction and deposited there. As these transfer tasks are executed, it is advantageous, but not absolutely necessary, for each of the objects to be identified or otherwise characterized using the characterization tool 7.

Figure 3:
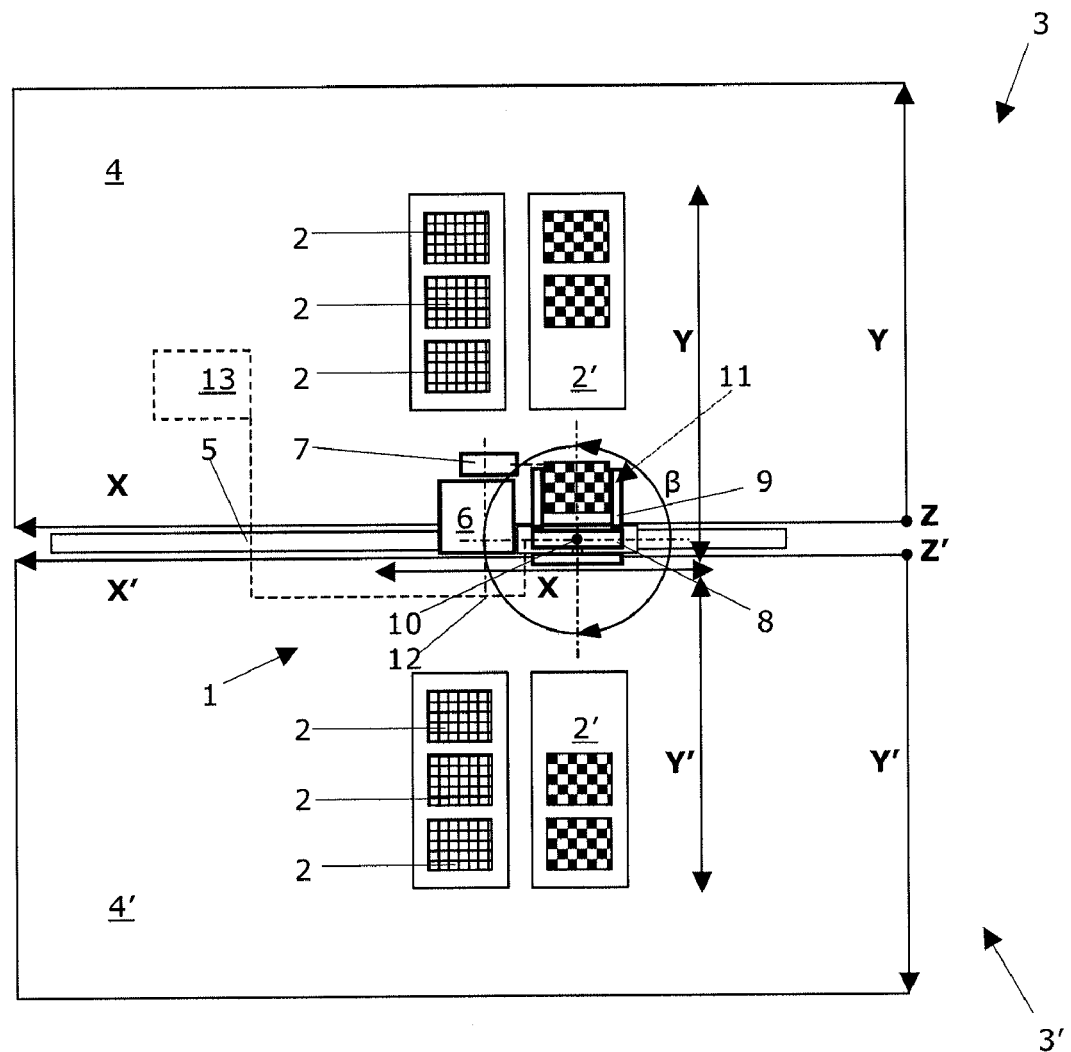
FIG. 3 shows a schematic top view of a second embodiment of a device according to the present invention.

FIG. 3 shows a schematic top view of a second embodiment of the device 1 according to the present invention for characterizing objects 2 in a sample manipulation system 3, in which the objects 2 are positioned on at least one essentially horizontal work field 4 having a lengthwise dimension X and a transverse dimension Y. This device 1 includes at least one rail 5 extending parallel to the X direction and at least one displacement unit 6, which is movable back and forth in the X direction on this rail 5 using drives, preferably having a tool 7 for characterizing an object 2 and a motorized gripping mechanism 8 for grasping and moving an object 2 toward the characterization tool 7. In addition, the device 1 includes a processor 13 for controlling the movements of the displacement unit 6 and the actions of the gripping mechanism 8 and for processing the information provided by the characterization tool 7, if necessary. The device 1 according to the present invention is distinguished in that the displacement unit 6 includes a carrying device 9, movable together therewith along the rail 5, for transferring objects 2 in the X direction. According to this second, preferred embodiment, the carrying device 9 includes a carrying plate 11 implemented for carrying objects 2, 2' and a gripping mechanism 8 for grasping objects 2 at a receiving location, for conveying these objects 2 onto the transfer plate 11, and for depositing these objects 2 at a delivery location. In this case, the receiving location may be located in a work field 4 on a first work platform and the delivery location may be located in a work field 4' of the first work platform or a second work platform.

The gripping mechanism 8 is preferably extendable in the Y direction over at least the dimension of an object 2, 2' positioned on the work field 4 and is implemented as a telescopic arm or articulated arm. In addition, the rail 5 is preferably positioned outside the work field 4 and has a length which corresponds to at least the lengthwise dimension X of the work field 4. The rail 5 may, however, also be implemented as longer than the work field 4 of the sample manipulation system 3. This makes it possible for objects to be retrieved from outside this sample manipulation system 3 and positioned on the work field 4. In addition, the delivery of objects which are to be removed from the work field 4 and to be deposited outside the sample manipulation system 3 is made possible.

A device 1, in which the carrying device 9 is rotatable around an angle β, which is preferably +180° and/or −180°, in relation to a Z axis 10, which is perpendicular to the horizontal work field 4, is especially preferred. In this case, two sample manipulation systems 3, 3', which are positioned parallel to one another and at the same working height (cf. FIG. 3), may be operated using only one device. In this case as well, the characterization tool 7 may include a barcode reader and/or an IR thermometer and/or a spectroscope and/or a tube inspection unit and/or a camera.

Figure 4:
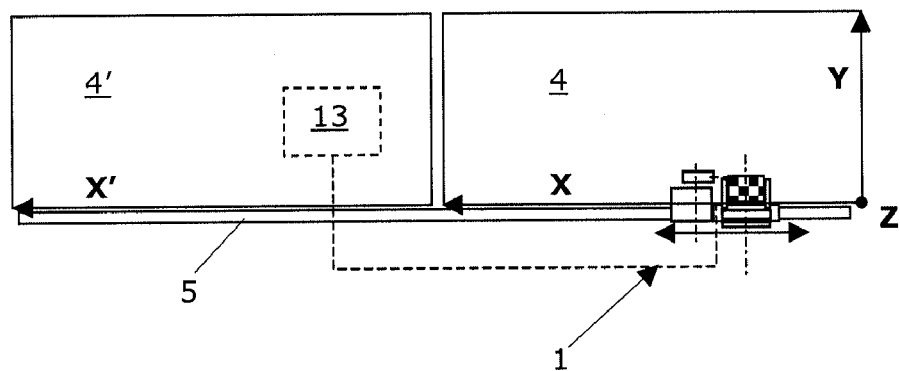
FIG. 4 shows a schematic top view of a third embodiment of a device according to the present invention.

The present invention also relates to sample manipulation systems 3 having at least one of the devices 1 described up to this point. Such systems may be implemented as a single work platform and may comprise a single work field 4 or two (or more) essentially horizontal work fields 4, 4', each having a lengthwise dimension X, X' and a transverse dimension Y, Y'. In this case, these work fields 4, 4' are preferably positioned in one plane and parallel to one another. An especially space-saving, mirror-symmetric arrangement of the work fields 4, 4', as in FIG. 3 and/or even an arrangement of the work fields 4, 4' aligned in the same direction, as in FIG. 4 comes into consideration.

In addition, more than two work platforms may be combined into a higher-order system. In particular, the linear arrangement of a larger work platform between two smaller work platforms allows the setup of a loading station (first smaller work platform) at one narrow side of a large work platform for processing and/or analyzing samples and the setup of an unloading station (second smaller work platform) at the other narrow side of the large work platform (not shown). Using this preferred arrangement, a system for processing samples having a high throughput and continuous loading and/or unloading may be provided. If desired, a lock may be provided between the smaller and the larger work platforms—either on one or both sides—via which lock objects 2 may preferably be transferred using the device according to the present invention.

The work fields 4, 4' may, however, also be positioned parallel to one another or one over another rotated by practically any arbitrary angle β (not shown). A further combination possibility of two work fields 4, 4' (not shown) is for them to be placed in two work platforms, which are positioned parallel one behind another, so that the rear of the first platform is opposite the front of the second platform. Using the device 1 according to the present invention, which is preferably positioned at the rear of the second platform in such cases, the front work field may be accessed "through the rear work field 4'". An additional combination possibility of two work fields 4, 4' (not shown) is for them to be placed parallel one behind another, so that the rear of the first platform is opposite the front of the second platform. Using the device 1 according to the present invention, which is preferably positioned at the rear of the first platform in such cases, the front and/or the rear work platform may be accessed without rotation.

The displacement unit 6 having the optional characterization tool 7 and the motorized gripping mechanism 8 is then movable back and forth using drives on at least one rail 5, which is positioned between the two work fields 4, 4' and extends parallel to the X direction and/or X' direction. The displacement unit 6 having the characterization tool 7 and the motorized gripping mechanism 8 may also be positioned such that it is movable back and forth on two rails 5 (not shown).

The present invention also includes corresponding methods for transferring and preferably also for characterizing objects 2 in one or more sample manipulation systems 3, objects 2 being grasped at a first X/Y position using the gripping mechanism 8, moved toward the characterization tool 7, characterized and/or identified by this characterization tool 7, transferred in the X direction, and deposited again at a second X/Y position. For this purpose, according to a first embodiment, the objects 2 are pulled onto a plate 11 of a carrying device 9 and transferred in the X direction on this carrying plate 11. According to a second embodiment, the objects 2 are raised using a gripping mechanism 8 and transferred in the X direction using this gripping mechanism 8. If the characterization and transfer method according to the present invention is used on a system which includes two or more work fields 4, 4', objects 2, 2' may be grasped at a first X/Y position in a first work field 4 and deposited at a second X/Y position in a second work field 4', which is preferably positioned parallel to the first work field 4 and above, below, or next to it. Objects 2, 2' may also be received and/or delivered outside the first or second work field 4, 4'.

To execute the method in a sample manipulation system 3 having work fields 4, 4' positioned as shown in FIG. 3, the carrying device 9 is rotated—between the grasping and depositing of an object 2, 2'—around an angle β, which is preferably +180° and/or −180°, in relation to a Z axis 10, which is perpendicular to the horizontal work field 4. In this case, a single microplate (as shown) or even an entire carrier having, for example, three microplates or racks having 16 sample tubes, for example (both not shown) may be transferred from a first work field 4 to a second work field 4'.

As an alternative to the illustration in the figures shown, the tool 7 for characterizing an object 2, 2' may include an IR thermometer and/or a spectroscope and/or a tube inspection unit and/or a camera, so that the identity and quality of a sample, its chemical composition, and/or its physical parameters may be detected using these tools. In this case, a device for performing an automatic transmission measurement on samples (e.g., blood samples in tubes) is referred to as a tube inspection unit. In this way, using the device according to the present invention, the presence, position, and quality of samples may be determined. Typical barcode readers include a 1-D barcode. However, those readers which read a 2-D code (e.g., in the form of a pixel surface) or a 3-D code (e.g., in the form of a relief or hologram) may also be used. The characterization tool 7 is preferably rotatable/tiltable around one or more axes, so that the sample container and/or objects 2, 2' may be observed or detected from different spatial angles. As a replacement for the tilt or rotational axes, which may be located in practically any arbitrary spatial position, a horizontal tilt axis 12 is shown in each of FIGS. 2 through 4.

All figures show only one device 1, however, it may be advantageous—above all if multiple work fields 4, 4' must be supplied—for the system to include two or more devices 1 for transferring and possibly characterizing objects 2.

The reference numbers in FIGS. 1 through 4 each identify identical features, even when all features are not expressly noted for every figure. Parts of the device 1 and the sample manipulation system 3 which anyone skilled in the art would select as desired to complete them, e.g., pipette tips, tubing which connects the pipette tips to the pumps, drives for the robot manipulators and the like, have been left out in the figures so that they are clearer. Such parts are, of course, part of the devices 1 and/or systems 3 according to the present invention. Any arbitrary combinations of the features disclosed of the present invention are included in its scope.

A variation of a sample manipulation system 3 (not shown in greater detail) preferably includes at least one work field 4, 4' or one work platform, which is designed as a protected region inaccessible to people. Such a protected region may include a flow cabinet or a partial vacuum chamber known per se and protects any people possibly present from contamination (biohazard) due to samples to be processed. A protected region of this type preferably includes a lock, via which objects 2 or samples may be transferred into or out of the flow cabinet, for example. The device 1 according to the present invention may be implemented as a part of this lock and/or execute its transfer function for this purpose.

The protected region of a work field may also be separated from the remainder of a work platform or a system so that a person may not touch or even damage especially sensitive parts. For example, unintended misalignment of a multi-pipette head (having 1536 extremely precisely adjusted pipetting needles, for example) or even a slight displacement of a high-precision carrier may have fatal effects, so that the pipetting needles may be damaged by touching the microplate surface. In addition, contamination or cross-contamination of neighboring samples in a 1536-well microplate, for example, would be a danger. Other misalignments could cause blocking of method sequences or contribute to confusion of samples.

Combinations and/or variations of the embodiments disclosed which appear advisable to those skilled in the art are also a component of the present invention.

What is claimed is:

1. A liquid handling work platform comprising:
   a) an essentially horizontal work field with a lengthwise dimension in the X direction and a transverse dimension, running in the Y direction, essentially perpendicularly thereto;
   b) at least one device for transferring objects, this device including at least one rail extending parallel to the X direction and a displacement unit, which is movable back and forth in the X direction on this rail using drives, and a motorized gripping mechanism for grasping an object;
   c) a barcode reader positioned on the displacement unit and implemented to read identification marks or flags of specimen carriers essentially vertically from the rear of the work field in a first passage and to identify the actual content of objects on these specimen carriers or in a specimen container in a second passage, in that the barcode reader is rotatable/tiltable around one or more axes; and
   d) a processor for controlling the movements of the displacement unit, the actions of the gripping mechanism and the identity of the samples and/or the objects as well as their X/Y positions,
   wherein the displacement unit includes a carrying device, movable together therewith along the rail, for transferring objects or specimen carriers in the X direction, this carrying device being implemented as a plate for carrying objects moved onto this carrying plate using the gripping mechanism.

2. The liquid handling work platform according to claim 1, wherein the carrying device, together with its carrying plate and its gripping mechanism, is rotatable around an angle β in relation to a Z axis that is perpendicular to the horizontal work field.

3. The liquid handling work platform according to claim 1, wherein the rail is positioned outside the work field and has a length which corresponds to at least the lengthwise dimension in the X direction of the work field.

4. The liquid handling work platform according to claim 1, wherein the gripping mechanism is extendable in the Y direction over at least the dimension of an object positioned on the work field.

5. The liquid handling work platform according to claim 1, wherein the device for transferring objects includes a tool for characterizing objects, the motorized gripping mechanism being implemented for grasping and moving an object toward this characterization tool and the processor for controlling the movements of the displacement unit and the actions of the gripping mechanism also being implemented for processing the information provided by this characterization tool.

6. The liquid handling work platform according to claim 1, wherein the characterization tool includes at least one of an IR thermometer, a spectroscope, a tube inspection unit, and a camera.

7. The liquid handling work platform according to claim 1, having two essentially horizontal work fields, wherein the displacement unit is movable back and forth using drives together with the transfer plate and the motorized gripping mechanism on at least one rail, which is positioned behind these work fields and extends parallel to the X direction.

8. The liquid handling work platform according to claim 7, wherein these work fields are aligned identically next to one another or aligned mirror-symmetric one behind another.

9. The liquid handling work platform according to claim 7, wherein these work fields are all positioned parallel to one another and in one plane.

10. A method for transferring objects in a liquid handling work platform that comprises:
    a) providing an essentially horizontal work field with a lengthwise dimension in the X direction and a transverse dimension, running in the Y direction, essentially perpendicularly thereto;
    b) providing at least one device for transferring objects, this device including at least one rail extending parallel to the X direction and a displacement unit, which is movable back and forth in the X direction on this rail using drives, and a motorized gripping mechanism for grasping an object;
    c) providing a barcode reader positioned on the displacement unit, which is rotatable/tiltable around one or more axes and implemented to identify the actual content of objects on specimen carriers or in a specimen container; and
    d) providing a processor for controlling the movements of the displacement unit, the actions of the gripping mechanism and the identity of the samples and/or the objects as well as their X/Y positions,
    the method further comprising the following steps:
    1) positioning of objects on at least one essentially horizontal work field in a first X/Y position;
    2) reading identification marks or flags of specimen carriers or objects essentially vertically from the rear of the work field in a first passage using the barcode reader;
    3) identifying the actual content of objects on these specimen carriers or in a specimen container in a second passage using the barcode reader and grasping the identified objects at the first X/Y position using the gripping mechanism;

4) moving the identified and grasped objects onto a plate of the carrying device;

5) transferring the identified and grasped objects in the X direction on this carrying plate; and 6) depositing the identified, grasped, and transferred objects again at a second X/Y position on an essentially horizontal work field.

11. The method according to claim 10, wherein grasping of an object and identifying is carried out at a first X/Y position in a first work field and depositing of this object is carried out at a second X/Y position in the same work field or a second work field that is positioned parallel to the first work field.

12. The method according to claim 10, wherein the carrying device, between the grasping and depositing of an object, is rotated around an angle β in relation to a Z axis that is essentially perpendicular to the work field.

13. The method according to claim 12, wherein the angle β, around which the carrying device is rotatable, is +180° and/or −180°.

14. The method according to claim 10, wherein the objects are moved toward a tool for characterizing an object and are characterized by this characterization tool, the information provided by the characterization tool being processed by a processor of the device.

15. The method according to claim 14, wherein by using the characterization tool, the chemical composition and the physical properties of samples is or are determined.

16. The liquid handling work platform according to claim 1, wherein the barcode reader is implemented for reading a 1-D, or 2-D, or 3-D code.

17. The liquid handling work platform according to claim 2, wherein the angle β, around which the carrying device is rotatable, is +180° and/or −180°.

* * * * *